US00PP34903P2

(12) United States Plant Patent
Boches et al.

(10) Patent No.: US PP34,903 P2
(45) Date of Patent: Jan. 10, 2023

(54) BLUEBERRY PLANT NAMED 'FC11-164'

(50) Latin Name: ***Vaccinium corymbosum* L.**
Varietal Denomination: FC11-164

(71) Applicant: Fall Creek Farm and Nursery Inc., Lowell, OR (US)

(72) Inventors: Peter Stefan Boches, Hilo, HI (US); Adam Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 17/891,580

(22) Filed: Aug. 19, 2022

Related U.S. Application Data

(60) Provisional application No. 63/238,966, filed on Aug. 31, 2021.

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

PP15,103 P3 8/2004 Hancock
PP24,661 P3 7/2014 Brazelton

OTHER PUBLICATIONS

CPVO Register. citation for Fc11-164. retrived Sep. 10, 2022. https://online.plantvarieties.eu/publicConsultationDetails?registerId=20221344&denomination=FC11-164&order=denomination&reverse=trueCPVO Register. citation for FC11-164. retrived Sep. 10, 2022. 1 page. (Year: 2022).*

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

The new blueberry plant variety 'FC11-164' is provided. 'FC11-164' is a commercial variety for hand and machine harvest fresh market. The new blueberry plant originated from open pollination of 'ZF06-168' (female parent) and an unknown male parent. 'FC11-164' is characterized for its upright growth habit, exhibits a high leaf length to width ratio, and produces a long leaf internode length.

6 Drawing Sheets

Latin name of the genus and species: Genus—*Vaccinium*. Species—*corymbosum* L.

Variety denomination: The new blueberry plant claimed is of the variety denominated 'FC11-164'.

BACKGROUND OF THE INVENTION

The present invention relates to the discovery of a new and distinct cultivar blueberry plant (*Vaccinium corymbosum* L.), referred to as 'FC11-164,' as herein described and illustrated. The new blueberry plant variety 'FC11-164' is a commercial variety.

Pedigree and History: The new blueberry plant originated from an open pollination cross of 'ZF06-168' (female parent, not patented) by an unknown male parent. The open pollination cross that produced 'FC11-164' was completed at Lowell, Oreg., USA in 2008. The new variety of 'FC11-164' was planted in 2009 in Lowell, Oreg. and selected in 2011.

'FC11-164' has been found to undergo asexual propagation in Lowell, Oreg. since 2012 by a number of routes, such as in vitro propagation. Asexual propagation techniques in Lowell, Oreg., such as in vitro propagation, have shown that the characteristics of the new variety are homogenous, stable, and strictly transmissible by such asexual propagation from one generation to another. Accordingly, the new variety undergoes asexual propagation in a true-to-type manner.

SUMMARY OF THE INVENTION

'FC11-164' is a commercial variety intended for the fresh fruit market. 'FC11-164' are low-medium vigor and upright with high productivity. The fruit is extremely crunchy with large size and excellent long term storage qualities. The following characteristics of the new cultivar have been repeatedly observed and are determined to be the unique characteristics of the new blueberry plant variety 'FC11-164':

1) Upright growth habit
2) High leaf length to width ratio
3) Long leaf internode length The new variety of the present invention can readily be distinguished from its ancestors. More specifically, the new variety provides berries with a crunchier texture and better long-term storage quality compared to the 'ZF06-168' variety (i.e., seed parent). The new variety can also be distinguished from other similar varieties. For instance, the new variety of the present invention can readily be distinguished from the 'Cargo' variety (U.S. Plant Pat. No. 24,661) as the new cultivar produces larger fruit size and has less vigor compared to the 'Cargo' variety.

BRIEF DESCRIPTION OF THE DRAWINGS

The accompanying photographic illustrations show typical specimens in full color of the foliage and fruit of approximately three to four-years old plants the new variety 'FC11-164'. The colors are as nearly true as is reasonably possible in a color representation of this type.

DETAILED BOTANICAL DESCRIPTION

Figure 1:
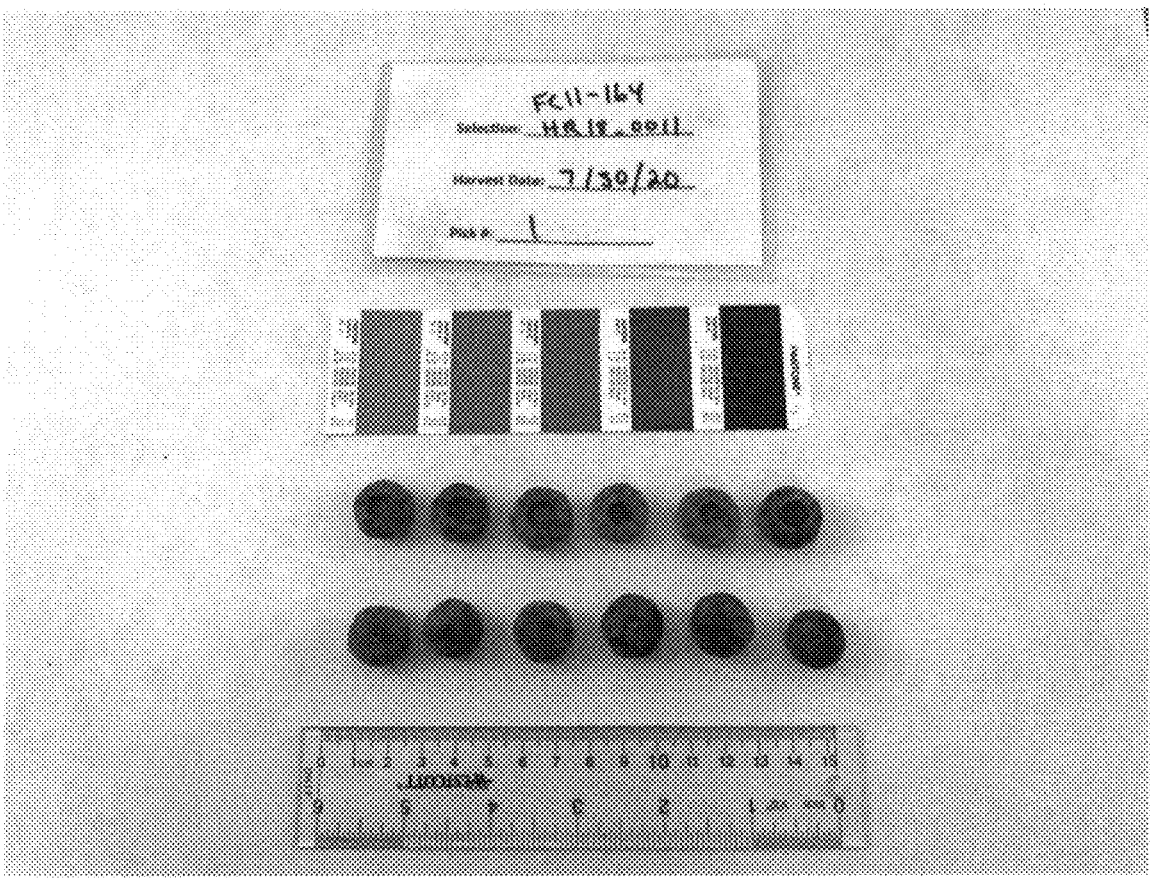
FIG. 1—depicts fruit with scale and Pantone colors of 'FC11-164' grown in Lowell, Oreg., USA and photographed on Jul. 30, 2020.
Figure 2:
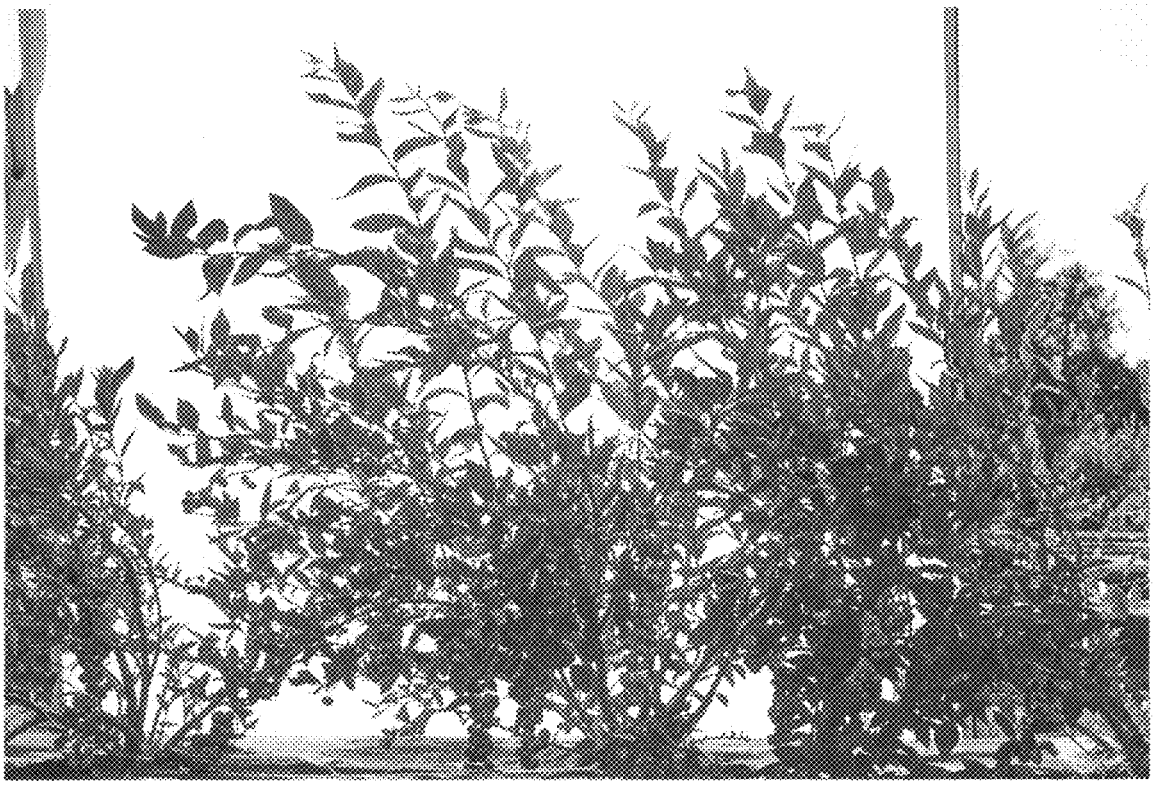
FIG. 2—depicts a plant showing the long internodes and plant shape of 'FC11-164' grown in Lowell, Oreg., USA and photographed on Aug. 3, 2020.
Figure 3:
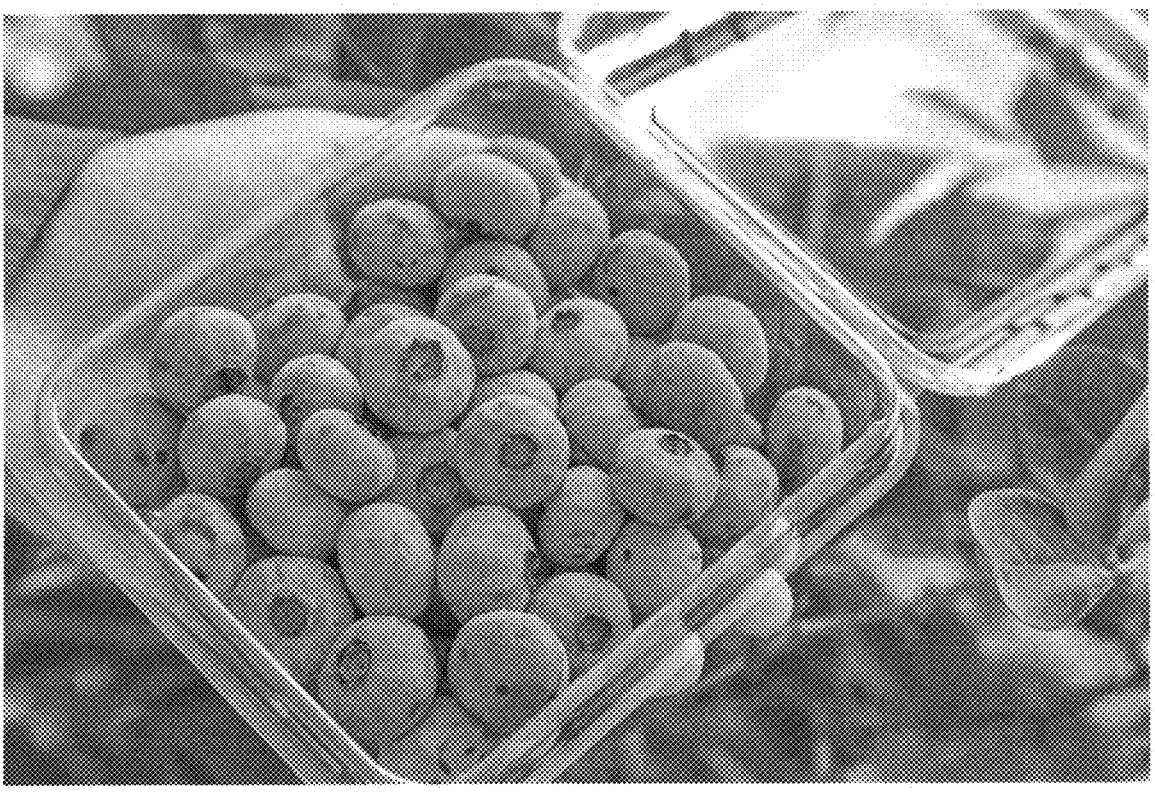
FIG. 3—depicts ripe fruit of 'FC11-164' grown in Lowell, Oreg., USA and photographed on Aug. 3, 2020.
Figure 4:
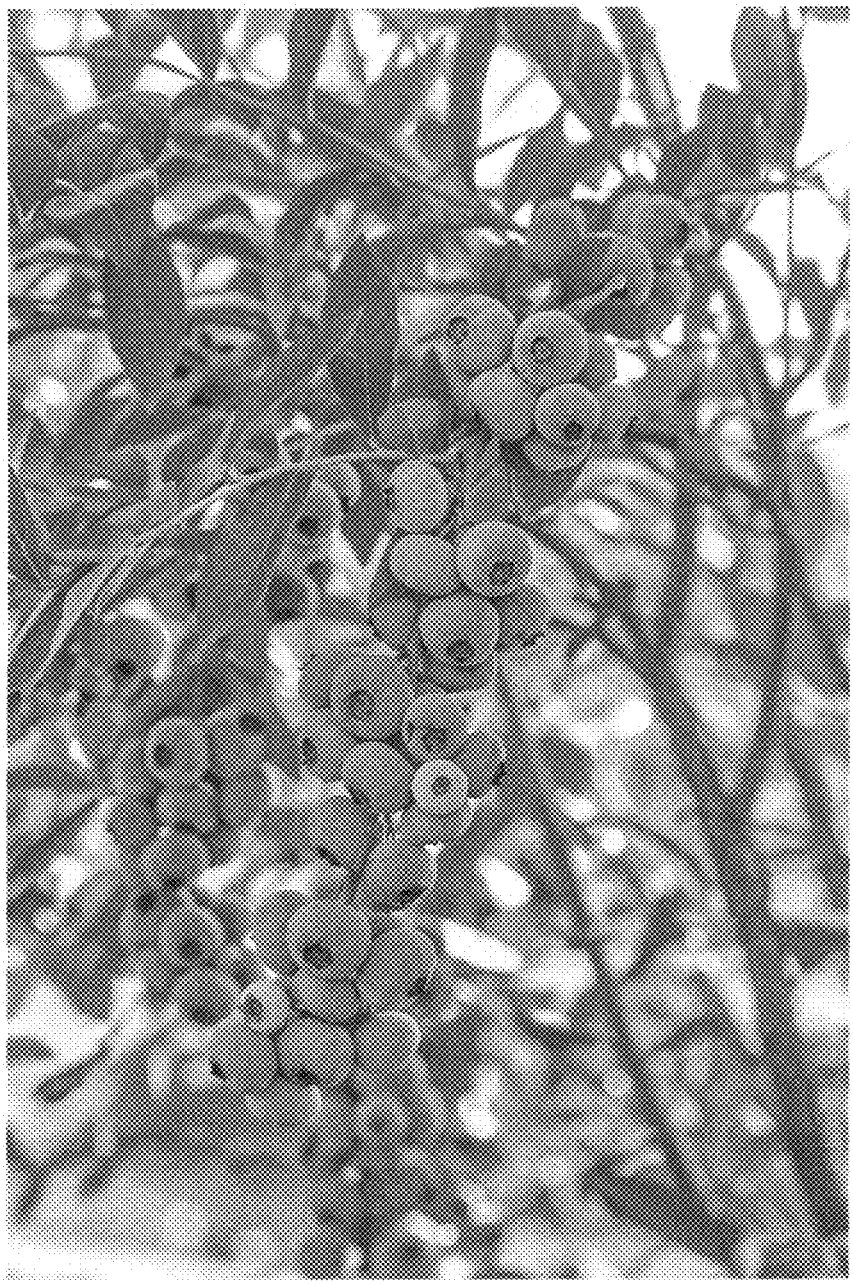
FIG. 4—depicts a ripe fruit cluster on the plant of 'FC11-164' grown in Lowell, Oreg., USA and photographed on Aug. 3, 2020.
Figure 5:
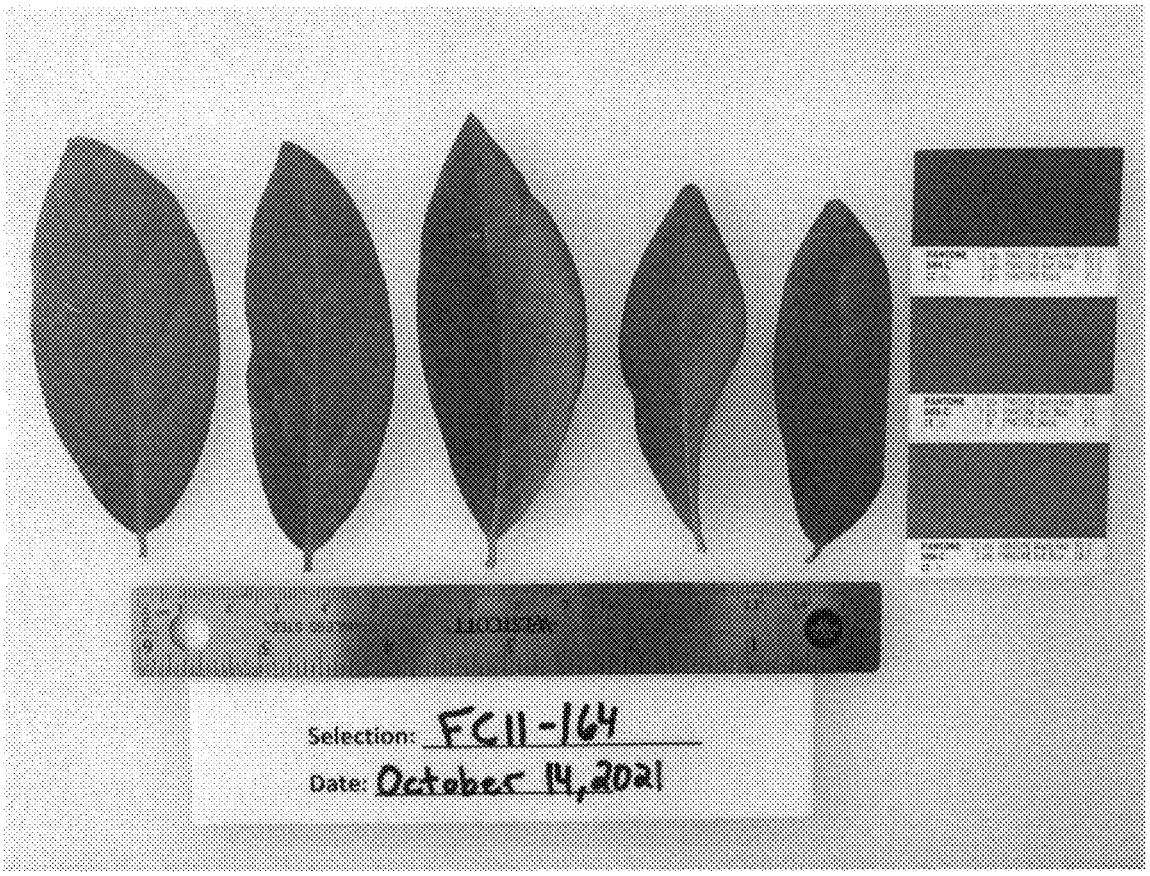
FIG. 5—depicts fall foliage with scale and Pantone colors of 'FC11-164' grown in Lowell, Oreg., USA and photographed on Oct. 15, 2021.
Figure 6:
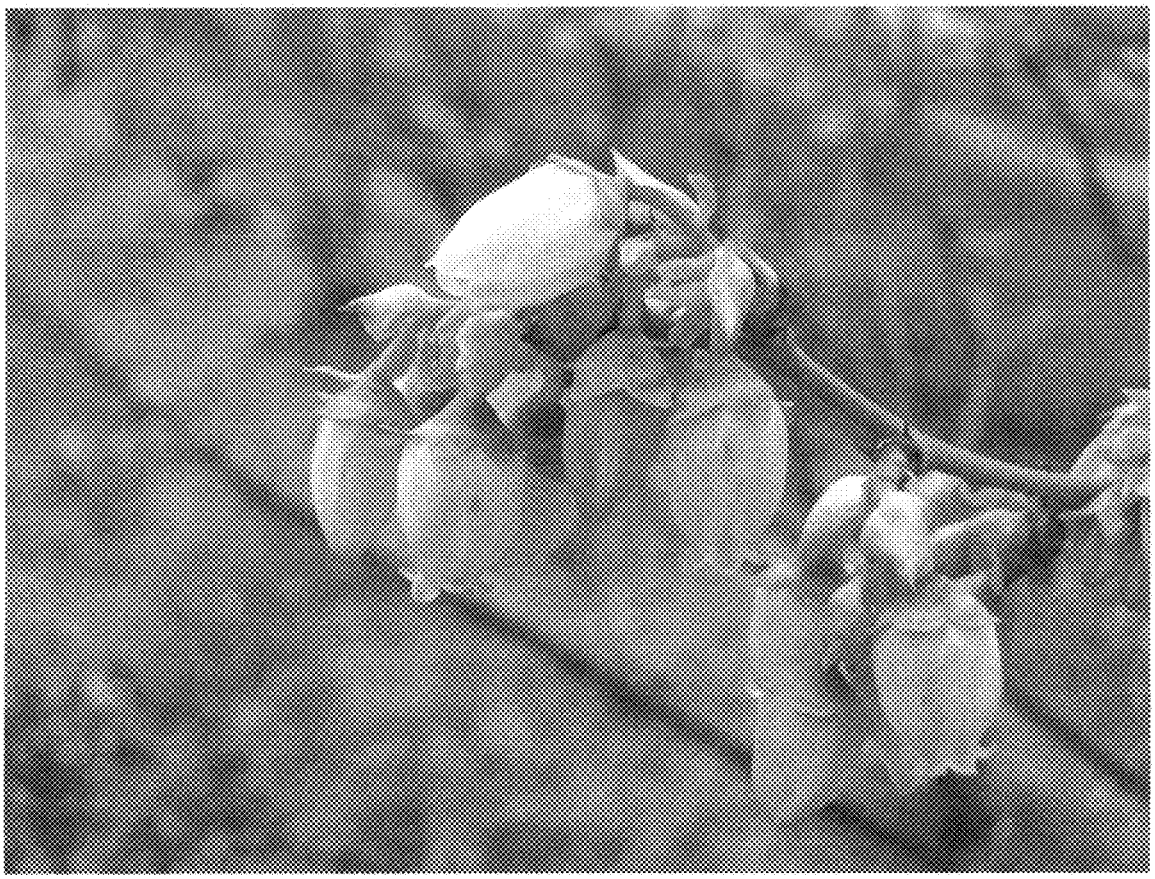
FIG. 6—depicts flowers on the plant of 'FC11-164' grown in Lowell, Oreg., USA and photographed on Apr. 18, 2018.

The following detailed description sets forth the distinctive characteristics of 'FC11-164'. The data which define these characteristics were collected from asexual reproductions ofthe original selection. Dimensions, sizes, colors, and other characteristics are approximations and averages set forth as accurately as possible. All measurements are the average of observations taken between 2018-2020. The plant history was taken on plants approximately 6 and 7 years of age, and the descriptions relate to plants grown in the field in Lowell, Oreg., USA. Descriptions of fruit characteristics were made on fruit grown in the field in Lowell, Oreg., USA. Color designations are from "The Pantone Book of Color" (by Leatrice Eiseman and Lawrence Herbery, Harry N. Abrams, Inc., Publishers, New York 1990). Where the Pantone color designations differ from the colors of the photographs, the Pantone colors are accurate.

VARIETY

Classification:
- *Family.*—Ericaceae.
- *Genus.*—*Vaccinium.*
- *Species.*—*corymbosum* L.
- *Common name.*—Northern Highbush Blueberry.

Parentage:
- *Female parent.*—'ZF06-168' (unpatented).
- *Male parent.*—Unknown (open pollination).

Market class: Commercial blueberry variety for hand and machine harvest fresh market.

PLANT

General:
- *Plant height.*—Average 1.64 m.
- *Plant width.*—Average 1.65 m.
- *Growth habit.*—Upright.
- *Growth.*—Low to medium vigor.
- *Productivity.*—Medium-high. Approximately 1.4 kg/plant on 3-4 year old plants compared to 1.8 kg/plant on 'Legacy' (not patented) and 1.1 kg/plant on 'Liberty' (U.S. Plant Pat. No. 15,146) for plants the same age.
- *Cold hardiness.*—Good. In Central and Northwest Washington, there has been no cold damage.
- *Cold tolerance.*—Not evaluated.
- *Chilling requirement.*—Estimated 800-1000.
- *Tolerance to disease.*—Not overly susceptible.
- *Leafing.*—Medium.
- *Twigginess.*—Very low.

STEM

General:
- *Suckering tendency.*—None.
- *Mature cane color.*—Moonlight 15-1309.
- *Mature cane length.*—159.00 cm.
- *Mature cane width.*—7.59 mm on a one-year-old cane.
- *Bark texture.*—Rough.
- *Fall color on new shoots.*—Bitter Chocolate 19-1317.
- *Surface texture of new wood.*—Smooth.
- *Internode length on strong, new shoots.*—26.28 mm.
- *Fruiting wood.*—32 cm in length.

FOLIAGE

General:
- *Time of beginning of leaf bud burst.*—Mid March.
- *Leaf color (top side).*—Chive 19-0315.
- *Leaf color (under side).*—Sage Green 15-0318.
- *Leaf arrangement.*—Alternate and spirally arranged: dextrose.
- *Leaf shape.*—Elliptic.
- *Leaf margins.*—Entire.
- *Undulation of margin.*—None.
- *Leaf venation.*—Anastomosing.
- *Leaf apices.*—Acute.
- *Leaf bases.*—Cuneate.
- *Leaf length.*—74.20 mm.
- *Leaf width.*—31.74 mm.
- *Leaf length/width ratio.*—High.
- *Leaf nectarines.*—Absent.
- *Pubescence of upper side.*—None.
- *Pubescence of lower side.*—None.
- *Cross sectional profile.*—Slight revolute.
- *Longitudinal profile.*—Flat.
- *Attitude.*—Porrect.
- *Fall leaf color.*—Bitter Chocolate 19-1317.

Petioles:
- *Length.*—4.96 mm.
- *Width.*—1.86 mm.
- *Color.*—Golden Green 15-0636.
- *Surface texture.*—Smooth.

FLOWERS

General:
- *Time of beginning of flowering.*—Approximately April 17$^{th}$.
- *Time of 50% anthesis.*—Mid April.
- *Flower shape.*—Urceolate.
- *Flower bud density.*—Medium.
- *Flower fragrance.*—Low to none, floral.
- *Immature flower color.*—Flamingo Pink 15-1821.

*Pollen staining.*—Not observed.
*Self-compatibility.*—The self-compatibility of 'FC11-164' is considered moderately compatible based on its comparison to 'Legacy' (not patented) self-compatibility that is very compatible.

Corolla:
*Color.*—Pearl 12-1304.
*Length.*—8.70 mm.
*Width.*—7.11 mm.
*Aperture width.*—3.64 mm.
*Anthocyanin coloration of corolla.*—Low.
*Corolla ridges.*—Present.
*Protrusion of stigma.*—0.63 mm.

Inflorescence:
*Length.*—25.02 mm.
*Diameter.*—24.52 mm.
*Length of peduncle.*—10.89 mm.
*Diameter of peduncle.*—Not observed.
*Surface texture of peduncle.*—Smooth.
*Color of peduncle.*—Faded Rose 18-1629.
*Length of pedicel.*—5.15 mm.
*Diameter of pedicel.*—Not observed.
*Surface texture of pedicel.*—Smooth.
*Color of pedicel.*—Peach Blossom 16-1626.
*Number of flowers per cluster.*—Average 6.7.
*Flower cluster density.*—Medium.

Calyx (with sepals):
*Diameter.*—7.74 mm.
*Color* (*sepals*).—Terra Cotta 16-1526.
*Calyx surface.*—Smooth.

Pistil:
*Length.*—9.57 mm.
*Ovary color* (*exterior*).—Peridot 17-0336.
*Style length.*—8.84 mm.

Stamen:
*Length.*—6.64 mm.
*Number per flower.*—10.
*Filament color.*—Asparagus Green 12-0311.

Anther:
*Length.*—4.15 mm.
*Number.*—2 per filament.
*Color.*—Inca Gold 17-1048.

Pollen:
*Abundance.*—Medium.
*Color.*—Cornhusk 12-0817.

FRUIT

General:
*Time of fruit ripening.*—Early July to mid August. Typical harvest time is during weeks 30-31.
*Time of* 50% *maturity.*—Average the beginning of July.
*Fruit development period.*—Average of 85 days from 50% bloom to 50% blue.
*Cluster density.*—Average 4.7 berries per cluster.
*Unripe fruit color.*—Bright Chartreuse 14-0445.
*Ripe berry color.*—Purple Cloud 16-3919.
*Berry surface wax abundance.*—Medium.
*Berry flesh color.*—Fog green 13-0210.
*Berry weight.*—2.66 grams.
*Berry height from calyx to scar.*—12.94 mm.
*Berry diameter.*—17.96 mm.
*Calyx aperture.*—6.92 mm.
*Calyx depth.*—Shallow.
*Pedicel length.*—5.15 mm.
*Pedicel surface texture.*—Smooth.
*Berry detachment force.*—Medium-Easy.
*Berry shape.*—Oblate.
*Fruit stem scar.*—1.86 mm.
*Berry flavor.*—Mild, sweet tart.
*Sweetness when ripe.*—Medium.
*Firmness when ripe.*—Very high.
*Acidity when ripe.*—Medium.
*Storage quality.*—Excellent, averaging 60 days.
*Suitability for mechanical harvesting.*—Excellent.
*Self-fruitfulness.*—Cross pollination is not required, however, fruit size will improve with cross-pollination.
*Uses.*—Fresh or process.

SEED

General:
*Seed abundance in fruit.*—Average.
*Seed color.*—Brown Sugar 17-1134.
*Seed dry weight.*—26.7 mg per 100 seeds.
*Seed length.*—1.5 mm.

COMPARISON BETWEEN NEW VARIETY AND COMMERCIAL CULTIVARS

TABLE 1

Comparison Table

| Denomination of similar variety | Characteristic for comparison | State of expression of similar variety | State of expression of candidate variety 'FC11-164' |
|---|---|---|---|
| 'Cargo' (U.S. Plant Pat. No. 24,661) | Shelf-life | Average | Excellent |
| 'Cargo' (U.S. Plant Pat. No. 24,661) | Fruit Size | Medium-Large | Large |
| 'Cargo' (U.S. Plant Pat. No. 24,661) | Vigor | Very High | Medium |
| 'Draper' (U.S. Plant Pat. No. 15,103) | Harvest season | Early-mid | Mid-late |
| 'Draper' (U.S. Plant Pat. No. 15,103) | Fruit Firmness | Average | Excellent |

The new blueberry plant variety 'FC11-164' has not been observed under all possible environmental conditions. The phenotype may vary somewhat with variations in environment and cultural practices such as temperature and light intensity without, however, any variance in genotype.

The invention claimed is:

1. A new and distinct variety of blueberry plant named 'FC11-164' substantially as illustrated and described herein.

* * * * *